United States Patent [19]
Hoetzel et al.

[11] Patent Number: 5,476,001
[45] Date of Patent: Dec. 19, 1995

[54] SENSOR FOR DETERMINING GAS COMPONENTS AND/OR GAS CONCENTRATIONS OF GAS MIXTURES

[75] Inventors: Gerhard Hoetzel, Stuttgart; Harald Neumann, Vaihingen/Enzweihingen; Johann Riegel, Bietigheim-Bissingen; Karl-Hermann Friese, Leonberg; Werner Gruenwald, Gerlingen, all of Germany

[73] Assignee: Robert Bosch GmbH, Stuttgart, Germany

[21] Appl. No.: 244,660

[22] PCT Filed: Dec. 7, 1993

[86] PCT No.: PCT/DE93/01164

§ 371 Date: Jun. 6, 1994

§ 102(e) Date: Jun. 6, 1994

[87] PCT Pub. No.: WO94/15206

PCT Pub. Date: Jul. 7, 1994

[30] Foreign Application Priority Data

Dec. 23, 1992 [DE] Germany ............... 42 43 734.2
Apr. 10, 1993 [DE] Germany ............... 43 11 849.6

[51] Int. Cl.⁶ .................. G01N 27/417; G01N 27/12; F02D 41/14
[52] U.S. Cl. ................................ 73/23.31; 73/118.1
[58] Field of Search ................... 73/116, 118.1, 73/23.2, 23.31, 23.32

[56] References Cited

U.S. PATENT DOCUMENTS

| | | | |
|---|---|---|---|
| 4,158,166 | 6/1979 | Isenberg | 324/29 |
| 4,543,273 | 9/1985 | Handa et al. | 73/23.2 |
| 4,553,424 | 11/1985 | Sakurai et al. | 73/23.2 |
| 4,750,353 | 6/1988 | Wright et al. | 73/118.1 |
| 4,927,517 | 5/1990 | Mizutani et al. | 204/406 |
| 4,961,341 | 10/1990 | Tanaka et al. | 73/118.1 |
| 5,071,626 | 12/1991 | Tuller | 73/23.31 |
| 5,223,783 | 6/1993 | Willis | 73/23.2 |
| 5,248,617 | 9/1993 | De Haan | 73/23.2 |
| 5,270,009 | 12/1993 | Nakamori et al. | 73/23.31 |

FOREIGN PATENT DOCUMENTS

| | | |
|---|---|---|
| 0142992A1 | 5/1985 | European Pat. Off. . |
| 0259175A2 | 3/1988 | European Pat. Off. . |
| 0257842A3 | 3/1988 | European Pat. Off. . |
| 0517366A1 | 12/1992 | European Pat. Off. . |
| 0517364A2 | 12/1992 | European Pat. Off. . |

OTHER PUBLICATIONS

J. H. Visser et al.: "Sensors for measuring combustibles in the absence of oxygen", vol. 9, 1992, pp. 233–239.

Logothetis et al, "Chemical and Physical Sensors based on oxygen pumping with solid state electrochemical cells," Sensors and Actuators, vol. 9, 1992, pp. 183–189.

*Primary Examiner*—Richard Chilcot
*Assistant Examiner*—George M. Dombroske
*Attorney, Agent, or Firm*—Spencer, Frank & Schneider

[57] ABSTRACT

A sensor for determining gas components and/or gas concentrations in gas mixtures, in particular in exhaust gases of internal combustion engines. The sensor has an oxygen pump cell and a measuring element having a sensitive region. Provided between the pump cell and the gas mixture is a diffusion path in which there are formed an oxygen gradient $X_{O2}$ and a gradient $X_{CO}$ of the gas component to be determined, which extend respectively in opposite directions. The measuring element is positioned relative to the pump cell and the diffusion path in such a way that an excess of oxygen is present on the sensitive region of the measuring element.

27 Claims, 6 Drawing Sheets

SENSOR FOR DETERMINING GAS COMPONENTS AND/OR GAS CONCENTRATIONS OF GAS MIXTURES

PRIOR ART

The invention proceeds from a sensor for determining gas components and/or gas concentrations in gas mixtures according to the generic concept of the main claim.

Sensors and Actuators B 9(1992), pages 233–239 discloses a sensor of the generic type for determining the CO concentration, in which a pump cell pumps oxygen to a measuring element. It has been found in this case that in the case of CO in air having 21% $O_2$ the resistance value of an $SnO_2$ semiconductor gas sensor is more than three orders of magnitude higher than in the case of CO in $N_2$. In this case, the measuring element is arranged in a measuring chamber without a defined reference to the pump cell or to the gas mixture. All that is required is for an adequate oxygen concentration to be present at the measuring element. The gas components to be measured in the gas mixture are designated below as pollutant components.

Furthermore, DE-OS 27 52 530 discloses a method for measuring the sum of all the combustible constituents in a total fuel atmosphere, in which method an electrochemical measuring cell and a pump cell are provided. The measuring cell sets the pumping potential to a level such that sufficient oxygen is pumped into the inner chamber in order in this way to cause a depletion in combustible constituents. Precisely as much oxygen is pumped in for a stoichiometric mixture always to be present at the measuring cell. The pumped flow is used in this case as a measure of the proportion of combustible constituents, the pumped flow being proportional to the rate of diffusion of the combustible constituents through the diffusion opening due to the conversion of the combustible constituents at the pump electrode. Because of the cross sensitivity with respect to oxygen, the reaction rate at the pump electrode provides no direct conclusion on the concentration of the combustible constituents in the exhaust gas.

Advantages of the invention

The invention utilizes the fact that given over-occupancy of the grain surfaces of the sensitive region of the measuring element with oxygen, even large changes in oxygen concentration have a negligibly small influence on the sensor signal. This dependence follows, for example, from FIG. 1a. The sensor according to the invention for determining gas components and/or gas concentrations in gas mixtures, in particular of CO, $NO_x$ and HC in exhaust gases of internal combustion engines, basically includes a measuring element which has a sensitive region, a pump cell with pump electrodes which are arranged on a solid electrolyte and cause a transfer of oxygen to the measuring element, and a diffusion path, in which a concentration gradient of the gas component to be determined and an concentration oxygen gradient are formed, provided between the pump cell and the gas mixture, and wherein the measuring element is positioned relative to the diffusion path such that an excess of oxygen is present in the sensitive region of the measuring element. Along the diffusion path, the two above mentioned gradients run counter to one another.

The sensor according to the invention has the advantage that it is possible to determine pollutant components and/or pollutant concentrations in gas mixtures independently of the oxygen partial pressure or of the lambda value of the gas mixture. The $O_2$ cross sensitivity is largely eliminated. A further advantage consists in that the sensor has a simple design and manages using measuring elements known per se. The measuring element is designed with a conventional pump cell in such a way that there is always an excess of oxygen at the measuring element.

Advantageous developments and improvements of the sensor specified above are possible and are described basic. It is particularly advantageous to set the pollutant concentration to a value at which the measuring element has a high sensitivity. This is performed in the case of a semiconductor gas sensor and of an electrochemical measuring cell by setting the pollutant concentration in such a way that a change in concentration delivers maximum sensitivity. This is the case with these sensor types when pollutant concentrations are low. FIG. 1b shows this dependence with the variation in the sensor signal S against the pollutant concentration in accordance with curve I for CO and HC and in accordance with curve II for $NO_x$. When a calorimetric sensor and an ionization detector are used, it is expedient to match the geometrical conditions (porosity, diffusion resistances) and the pump capacity in such a way that the oxygen concentration $XO_2$ at the location of the measuring element just exceeds the value required for the maximum pollutant concentration, in order for the measuring element to deliver a sufficiently high sensor signal. This emerges from FIGS. 1b and 1c. FIG. 1c illustrates that the sensor signal of calorimetric sensor rises linearly with the pollutant concentration. Consequently, given a constant oxygen partial pressure the sensor signal is highest for high pollutant concentrations XCO. However, in both cases it is a precondition for eliminating the oxygen cross sensitivity that the oxygen concentration $XO_2$ is higher than the stoichiometrically required value of the pollutant concentration.

A first advantageous embodiment is obtained when the pump cell and the measuring element form an integrated layer system (integrated sensor type). In the case of such an embodiment, the measuring element is a semiconductor gas sensor, for example. In this case, the pumped oxygen can transfer directly to the semiconducting metal oxide layer, for example $SnO_2$, via spillover effects of the $ZrO_2$ solid electrolytes by means of the platinum of the electrodes, without having to enter the gas phase in the process. It is possible in this way to influence the surface condition of the metal oxide (adsorbed oxygen) directly via the pump cell. The surface change of place is performed in this case substantially faster than a diffusion via the gas phase. Similar phenomena occur when an electrochemical measuring cell is used.

A further advantageous embodiment consists in spatially separating the pump cell and measuring cell (discrete sensor type). This arrangement has the advantage that the dimensioning of the diffusion channel is not subject to extremely close tolerances. The reproducibility of the sensor function is essentially determined by the accuracy with which the ratio of the channel length to the measuring element position can be met.

A particularly powerful pump cell is provided when the oxygen present at the oxygen pump cell is already present in molecular form inside the porous solid electrolyte body on the catalyzing pump electrodes. It is particularly advantageous for the purpose of feeding sufficient oxygen to the pump electrode to supply the oxygen to be pumped via a diffusion channel to the side of the porous solid electrolyte. It is, furthermore, expedient when the oxygen of the pump cell which is to be pumped is, in addition, supplied through an opening which is introduced in a cover layer and guided to the diffusion gap, as a result of which the diffusion resistance can be reduced.

An economic design is achieved by means of a laminate composite of ceramic foils, in which at least the resistance heater required to operate the sensor is integrated, it being the case that the use of electrically insulating $Al_2O_3$ ceramic foils has proved to be particularly suitable.

BRIEF DESCRIPTION OF THE DRAWINGS

Examplary embodiments of the invention are represented in the drawing and explained in more detail in the following description. In detail:

FIG. 3b shows a curve of the oxygen concentration and of the CO concentration against the length of the diffusion gap in accordance with the sensor in FIG. 3a;

FIG. 7b shows a sectional representation according to lines II—II in accordance with FIG. 7a; and FIG. 7c shows a sectional representation according to lines III—III in accordance with FIG. 7a.

DETAILED DESCRIPTION OF THE EXEMPLARY EMBODIMENTS

The sensor according to the invention can be implemented in principle by means of two sensor types;

A Sensors having a direct connection between the measuring element and pump cell (integrated sensor type), and B Sensors having spatial separation of the measuring element and pump cell (discrete sensor type).

Exemplary embodiments of an integrated sensor type A are represented in FIGS. 2a to 2c, 4a, 5a, 5b and 6a; discrete sensor types B follow from FIGS. 3a, 4b, 5d and 6b. Intermediate forms between the integrated and the discrete design are possible, for example in accordance with FIGS. 2d, 5c and 7a.

Figure 1B:
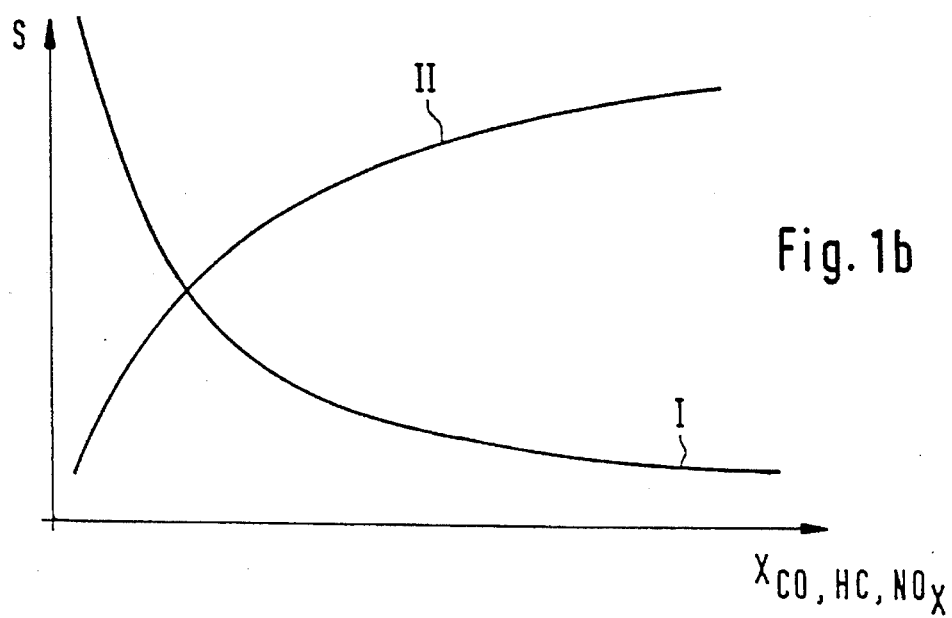
FIG. 1b shows the sensor signal against the pollutant concentration given a constant oxygen concentration.
Figure 1A:
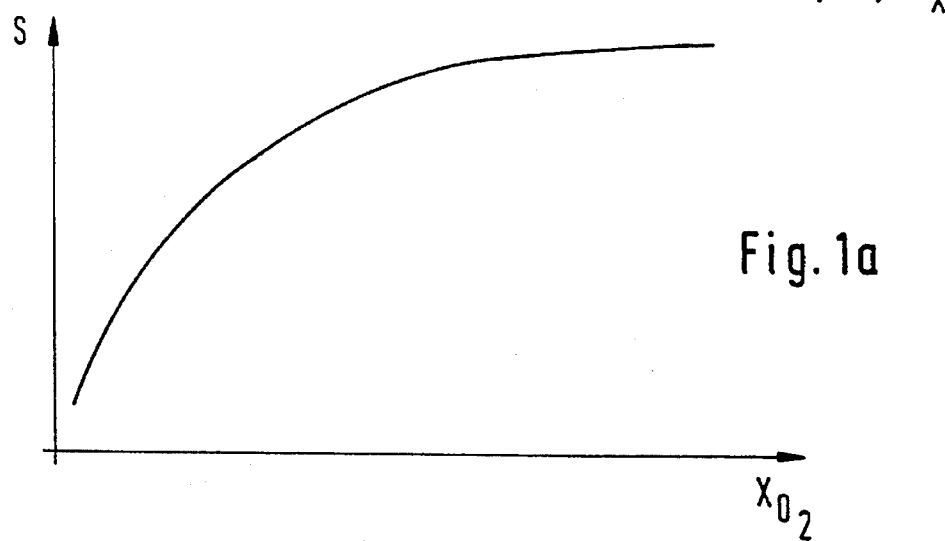
FIG. 1a shows the variation in the sensor signal against the oxygen concentration given a constant pollutant concentration.
Figure 1C:
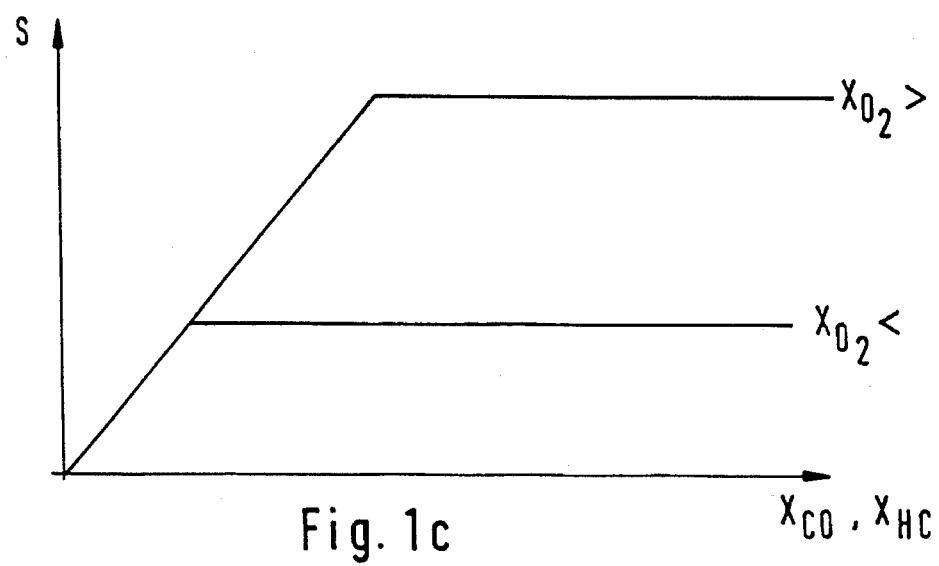
FIG. 1c shows the sensor signal of a colorimetric sensor as a function of the oxygen concentration and the pollutant concentration.
Figure 2A:
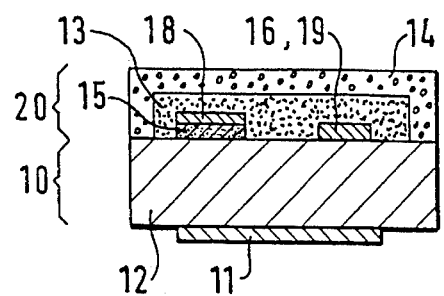
FIGS. 2a to 2d show sectional representations of integrated sensors having a pump cell and a semiconductor gas sensor.

A first embodiment of an integrated sensor type A is shown in FIG. 2a. The sensor consists of a pump cell 10 and a measuring element 20. The measuring element 20 is in this case a semiconductor gas sensor having a first and a second measuring electrode 18, 19 and a porous semiconducting metal oxide layer 13 which, for example, consists of $SnO_2$. A plate-shaped or foil-shaped solid electrolyte carrier 12 made from an $O_2$ ion-conducting solid electrolyte, for example from stabilized zirconium oxide, has an outer pump electrode 11 paragraph, on one large face, and an inner pump electrode 16 arranged, on the opposite large face. The two pump electrodes 11, 16 consist, for example, of platinum or platinum-cermet. An $Al_2O_3$ insulating layer 15, for example, is applied next to the inner pump electrode 16 on the same large face of the carrier 12. The measuring electrode 18 is located on the $Al_2O_3$ insulating layer 15. The metal oxide layer 13 is laid over the inner pump electrode 16 and the measuring electrode 18 in order to form the sensitive region, with the inner pump electrode 16 simultaneously forming the second measuring electrode 19. It is expedient for the purpose of protection against the exhaust gas if the metal oxide layer 13 is covered by a porous protective layer 14 which simultaneously acts as a diffusion barrier.

Figure 2B:
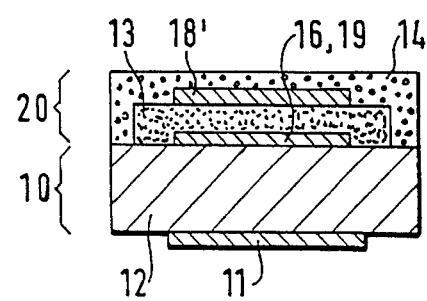

In accordance with a second embodiment represented in FIG. 2b of an integrated sensor, only the inner pump electrode 16 is located on the large face of the solid electrolyte carrier 12 opposite the outer pump electrode 11. The inner pump electrode 16 is simultaneously used as measuring electrode 19 for the measuring element 20. A second measuring electrode 18' is applied to the side, opposite the inner pump electrode 16, on the metal oxide layer 13, over which the protective layer 14 is laid. The measuring electrode 18' is hereby catalytically inactive, so that the pollutant components are not already oxidized on the measuring electrode 18'.

Figure 2C:
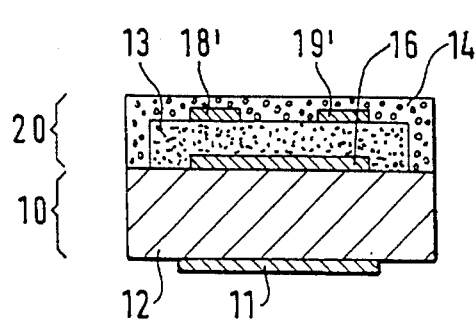

FIG. 2c shows a third embodiment of an integrated sensor having a four-electrode structure. In accordance with this, the inner pump electrode 16, which is positioned between the solid electrolyte carrier 12 and the metal oxide layer 13, has only a pumping function. Two measuring electrodes 18', 19' are arranged next to one another on the metal oxide layer 13 on the side opposite the inner pump electrode 16. The measuring electrodes 18', 19' are likewise covered by the protective layer 14. The measuring electrodes 18', 19' are likewise catalytically inactive for the reasons already mentioned.

An oxygen gradient and a pollutant gradient which respectively run in opposite directions build up in the porous metal oxide layer 13 in the said integrated sensor types in accordance with FIGS. 2a, 2b and 2c. The oxygen concentration decreases from the inner pump electrode 16 up to the gas mixture at the protective layer 14. The pollutant concentration, by contrast, has a maximum at the interface between the protective layer 14 and gas mixture, and decreases towards the inner pump electrode 16.

The sensors of integrated design can use the direct oxygen transfer to the metal oxide layer 13 via the spillover effect, directly from the $ZrO_2$ of the carrier 12 or by means of the platinum of the electrode 16. Consequently, a surface change of place can occur substantially faster than a diffusion of the oxygen via the gas phase. In addition, given a diffusion via the gas phase there is, furthermore, a need for a desorption step of the oxygen from the surface of the platinum pump electrode and for an adsorption step of the oxygen on the surface of the metal oxide semiconductor.

Figure 2D:
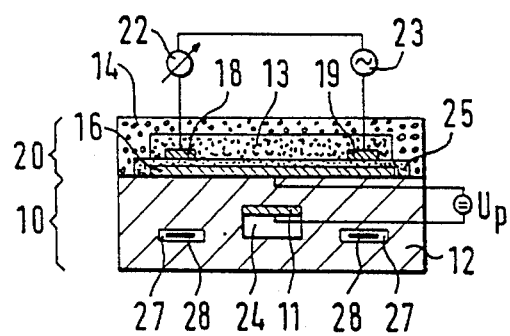

An exemplary embodiment of an intermediate form between an integrated sensor type and a discrete sensor type is represented in FIG. 2d. The sensor is shown with its electric connections with the aid of this representation. The design, known per se, of the pump cell 10 used in all the exemplary embodiments is also illustrated. Provided in the solid electrolyte 12 is a diffusion channel 24 in which the outer pump electrode 11 is arranged. Operation of the pump cell requires an operating temperature of, for example, at least 300° C., and for this purpose a heater 28 embedded in an insulation 27 is integrated in the solid electrolyte 12. Furthermore, a porous insulating layer 25 made from, for example, $Al_2O_3$ is arranged between the inner pump electrode 16 and the porous metal oxide layer 13. The oxygen pumped from the pump cell 10 to the inner pump electrode 16 thereby diffuses through the porous insulating layer 25 to the metal oxide layer 13.

Figure 2E:
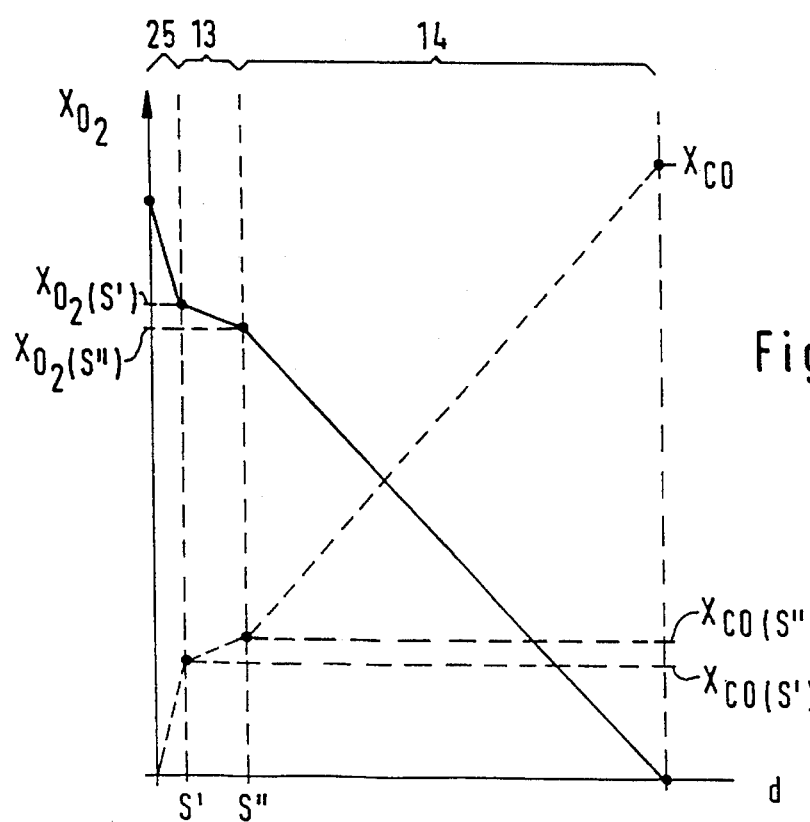
FIG. 2e shows a curve of the oxygen concentration and of the CO concentration in accordance with the sensor in FIG. 2d.

FIG. 2e shows the curve of the pollutant concentration XCO and the oxygen concentration $XO_2$ along the layer thickness d from the porous insulating layer 25, metal oxide layer 13 and protective layer 14 of the semiconductor gas sensor of the sensor type according to FIG. 2d. Accordingly, the pollutant concentration XCO(s') and XCO(s") at the two interfaces S' and S" of the metal oxide layer 13 is well below the oxygen concentration $XO_2$ (s') and $XO_2$ (s") at these points. The requirement of the invention that an excess of oxygen is present on the sensitive region of the measuring element 20 is thus met.

The mode of operation of the sensor according to the invention is to be explained by the example of the sensor type in accordance with FIG. 2d. Oxygen is pumped from the outer pump electrode 11 to the inner pump electrode 16 by applying a direct voltage $U_p$ to the pump electrodes 11 and 16. In this case, either the oxygen to be pumped can be extracted via the diffusion channel 24 from a reference gas located on the outer pump electrode side 11 of the pump cell 10, or the sensor is entirely immersed in the measuring gas, in order for molecular oxygen or oxygen from oxygen-containing compounds to be pumped out of the exhaust gas via the outer pump electrode 11. A measuring voltage source 23 and an ammeter 22 are also provided. The ammeter 22 serves, for example, to accept the sensor signal.

In accordance with a first mode of operation, the pumping voltage $U_p$ of the pump cell 10 is controlled at a constant oxygen partial pressure via known control circuits, as described, for example, in the SAE publication 86 04 08 and in Sensors and Actuators, 9 (1986), pages 287 to 300, on the inner pump electrode 16 of the pump cell 10. The oxygen partial pressure is set in this case in accordance with the invention to excess with respect to the partial pressure, to be measured, of the pollutant components. For example, the oxygen partial pressure is selected at between 2 and 10 % of the total pressure of the measuring gas. The constant oxygen partial pressure also corresponds to the oxygen partial pressure at the three-phase boundary of the inner pump electrode 16 and gas chamber if a catalytically inactive electrode material is used. If use is made of a catalytically active electrode, particularly one made from platinum, which sets an equilibrium, the reducing gas which reaches the three-phase boundary of the electrode and the pump cell by means of pore diffusion reacts with the oxygen. A pollutant gradient which depends on the concentration of the reducing pollutant component in the exhaust gas and which determines the conductivity of the metal oxide layer 13 integrally via the layer thickness thereof is set up from the exhaust gas to the pump electrode 16 through the metal oxide layer 13.

In accordance with a further mode of operation, a constant pumping current $I_p$ is used to pump a constant oxygen ion current to the three-phase boundary, which oxygen ion current sets up an excess of oxygen at the measuring element 20, likewise in accordance with the invention. Molecular oxygen diffuses into the exhaust gas through the porous metal oxide layer 13. An oxygen partial pressure which is determined by the pumping current, the oxygen partial pressure and the partial pressures of the pollutants in the gas mixture is set up at the three-phase boundary of the pump electrode 16.

Figure 3A:
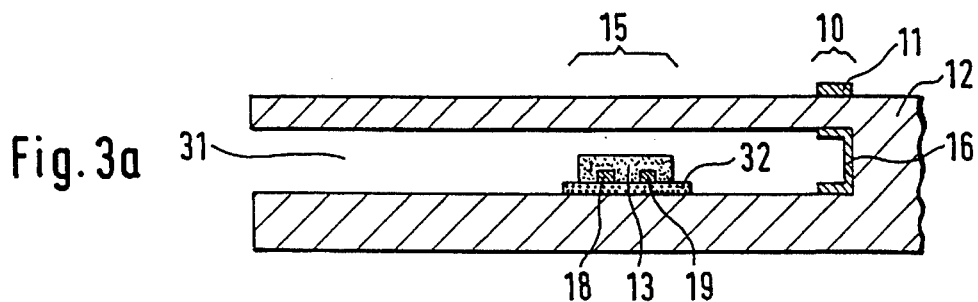
FIG. 3a shows a sectional representation through a discrete sensor having a pump cell and a semiconductor gas sensor.

An exemplary embodiment of a discrete sensor type is represented in FIG. 3a. A diffusion gap 31 is produced in a plate-shaped or foil-shaped solid electrolyte carrier 12 in a known way, for example by imprinting a material, such as carbon black or theobromine, which is destroyed without residue at a heightened temperature. The inner pump electrode 16, which is to have a large active surface as far as possible and therefore occupies the entire height of the diffusion gap 31 and is additionally extended in the longitudinal direction of the diffusion gap 31 on the top side and underside is arranged at the closed end of the diffusion gap 31. The outer pump electrode 11 is arranged opposite the inner pump electrode 16 on the upper large face of the solid electrolyte carrier 12.

The measuring element 20, for example a semiconductor gas sensor 15, is positioned at a distance s from the entrance to the diffusion gap 31. In addition, an insulating layer 32, for example made from $Al_2O_3$, on which the two measuring electrodes 18 and 19 and the metal oxide layer 13 are arranged, is applied to the lower face of the diffusion gap 31.

Figure 3B:
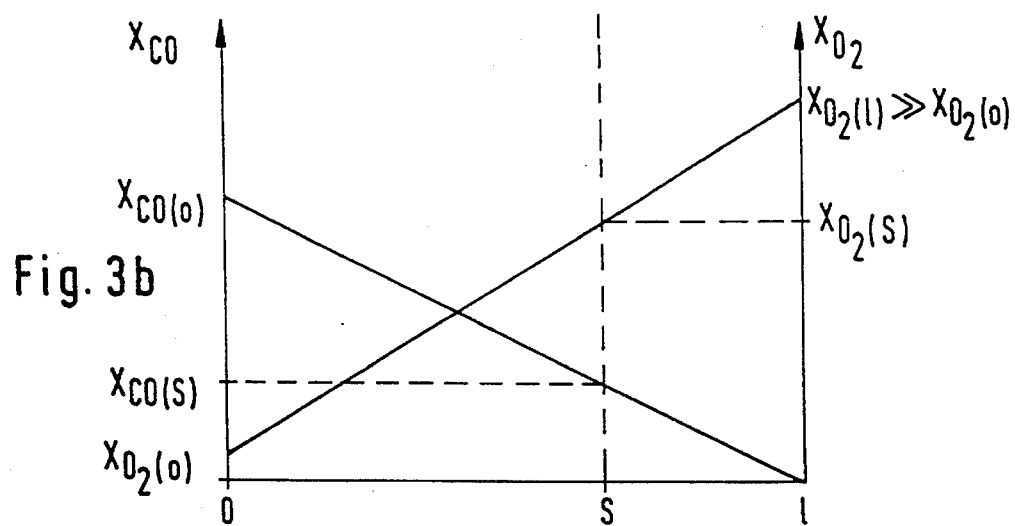

During operation of the sensor, a pumping voltage $U_p$ is applied to the electrodes 11 and 16 of the pump cell 10 in such a way that a defined, sufficiently high oxygen partial pressure is set up, for example 10% of the total pressure at the closed end of the diffusion gap 31. The oxygen partial pressure in the gas mixture at the opening of the diffusion gap 31 is negligibly small by comparison with this oxygen partial pressure. The curve of the oxygen concentration $XO_2$ and of the pollutant concentration XCO plotted against the length l of the diffusion gap 31 follows from FIG. 3b. The oxygen gradient $XO_2$ and the pollutant gradient XCO are oppositely directed. $XO_2(s) \gg XCO(s)$ at the point s in the diffusion gap 31 at which the semiconductor gas sensor 15 is arranged.

Given linear conditions, it holds for the partial pressure of the reducing component, for example CO, at the location s of the semiconductor gas sensor 15 that:

$$pCO(s)=(1-s/l)pCO$$

It is therefore ensured that the semiconductor gas sensor 15 is always exposed to an approximately constant oxygen partial pressure. It is possible to calculate back to the partial pressure of the reducing component in the gas mixture from the partial pressure of the reducing component, for example CO at the location of the sensor.

Discrete sensor types (B) have the advantage, in particular, that there is no need to take account of any extremely narrow tolerances in the dimensioning of the diffusion gap 31. The dimensioning of the diffusion gap 31 need only be adapted to the pump capacity of the pump cell 10 in such a way that it is possible to set the parameters of oxygen partial pressure equal to 2 to 10% and the partial pressure of the reducing pollutant component, for example CO, equal to 0 at the closed gap end.

Figure 4A:
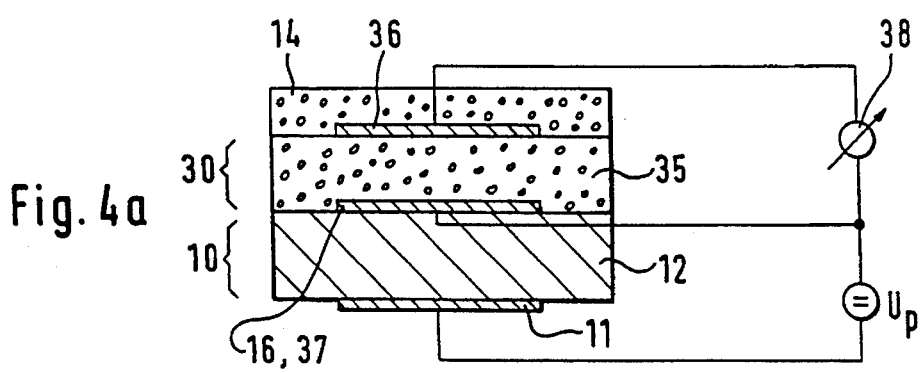
FIG. 4a shows a sectional representation through an integrated sensor having a pump cell and an electrochemical measuring cell.

An integrated sensor in which the measuring element 20 is an electrochemical measuring cell 30 follows from FIG. 4a. As in the semiconductor gas sensors described, the pump cell 10 has an inner and an outer pump electrode 11, 16. Arranged on the inner pump electrode 16 is a further solid electrolyte layer 35 on which a measuring electrode 36 is applied opposite the inner pump electrode 16. The solid electrolyte layer 35 is of porous design. The measuring electrode 36 is not catalytically active. A "mixing potential" which also depends on the pollutant components is measured only in the case of a catalytically weak or non-active measuring electrode. In the case of this sensor, as well, the measuring electrode 36 is covered by a porous protective layer 14. In order to form the measuring cell 30, the inner pump electrode 16 is simultaneously connected as a reference electrode 37.

The pollutant gradient and the oxygen gradient extend directed oppositely in each case in the porous solid electrolyte layer 35, the aim being to set an excess of oxygen at the reference electrode 37. The excess of oxygen at the inner pump electrode 16 and thus at the reference electrode 37 forms a corresponding potential difference between the reference electrode 37 and measuring electrode 36. The pumping voltage source $U_p$ which is further provided has the same function in this exemplary embodiment as in FIG. 2d. The potential difference is picked up as sensor signal by means of a voltmeter 38.

Figure 4B:
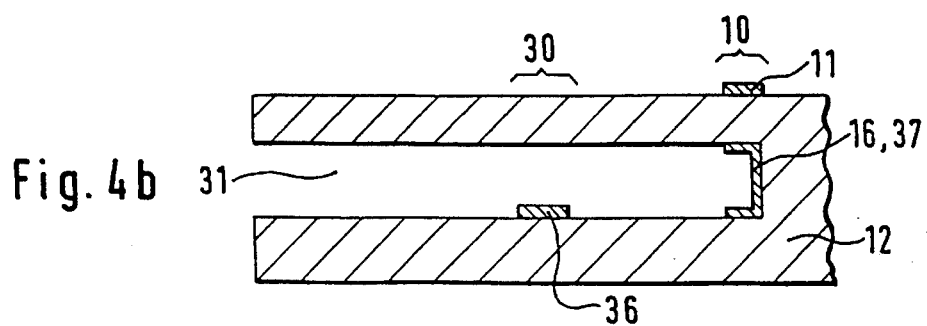
FIG. 4b shows a sectional representation through a discrete sensor having a pump cell and an electrochemical measuring cell.

An embodiment of a discrete sensor having an electrochemical measuring cell 30 is represented in FIG. 4b. This sensor is designed similarly to the sensor in FIG. 3a, the only point being that an electrochemical measuring cell 30 is provided instead of the semiconductor gas sensor. The measuring cell 30 consists of the measuring electrode 36 arranged in the diffusion gap 31 and of the reference electrode 37 formed by the inner pump electrode 16. The further design and the functioning correspond to the embodiment in FIG. 3a.

Figure 5A:
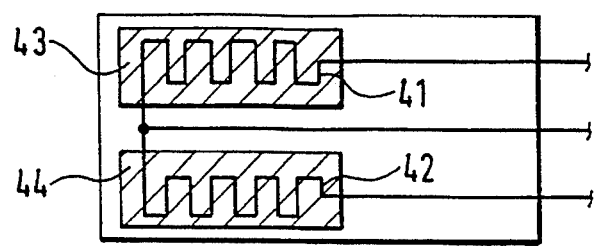
FIG. 5a shows a plan view of a calorimetric gas sensor.
Figure 5B:
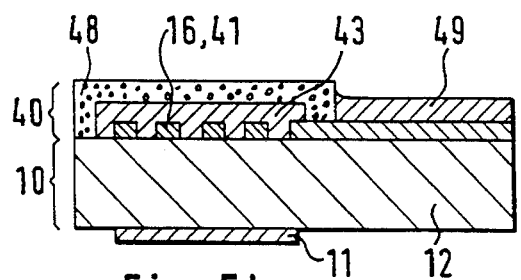
FIG. 5b and FIG. 5c respectively show a sectional representation of an integrated sensor consisting of a calorimetric gas sensor in accordance with FIG. 5a and of an $O_2$ pump cell.

A further exemplary embodiment of an integrated sensor is shown in FIGS. 5a and 5b, in which a calorimetric gas sensor 40 (heat-of-reaction sensor, Pellistor) is used as measuring element. For this purpose, there are applied to the solid electrolyte carrier 12 of the pump cell 10 a first and a second meandering resistor run 41 and 42 which respectively consist, for example, of platinum or platinum-cermet. Arranged on the first resistor run 41 is a porous catalytically active, electrically non-conductive layer 43, and on the second resistor run 42 a catalytically inactive, electrically non-conductive layer 44 (FIG. 5b).

The catalytically inactive layer 44 is preferably gas-tight, in order largely to avoid a catalytic reaction on the resistor run 42. The catalytically active layer 43 is expediently provided with a porous protective layer 48 which likewise acts as a diffusion barrier. It is advantageous to apply in the region of the resistor run supply leads a cover layer 49 which is gas-tight, insulating or insulated against the conductor tracks, and which prevents reactions on the supply lead. Oxidizable gases react with the oxygen of the air on the catalytically active layer 43 accompanied by the release of heat, the heat toning being measured either non-isothermally via the increase in temperature of the sensor or isothermally via the change in power loss of the sensor (control at constant sensor temperature). Given an excess of $O_2$, the heat toning is dependent only on the gas concentration of the oxidizable gases, but not on the $O_2$ concentration. It is necessary for this purpose to introduce a sufficiently high excess of $O_2$ into the catalytically active layer 43 by means of the pump cell 10.

Figure 5C:
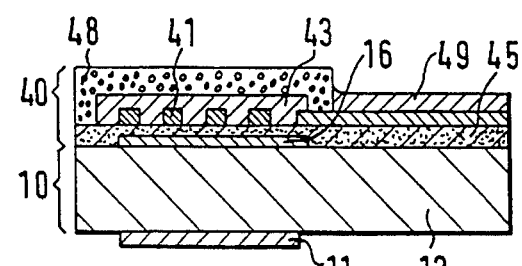

A mixed form between an integrated sensor type A and discrete sensor type B with its calorimetric sensor 40 follows from FIG. 5c. In this case, the pump cell 10 is designed with a separate inner pump electrode 16 over which a porous insulating layer 45 is laid. At least the resistor run 41 and the catalytically active layer 43 are applied to the porous insulating layer 45. The sensor of this embodiment works according to the same principle as the sensor represented in FIG. 5b. The oxygen gradient and the pollutant gradient respectively extend through the porous catalytically active layer 43 and the porous insulating layer 45. The porous protective layer 48 can be applied over the catalytically active layer. The resistor run supply lead is likewise advantageously provided with the gas-tight cover layer 49.

Figure 5D:
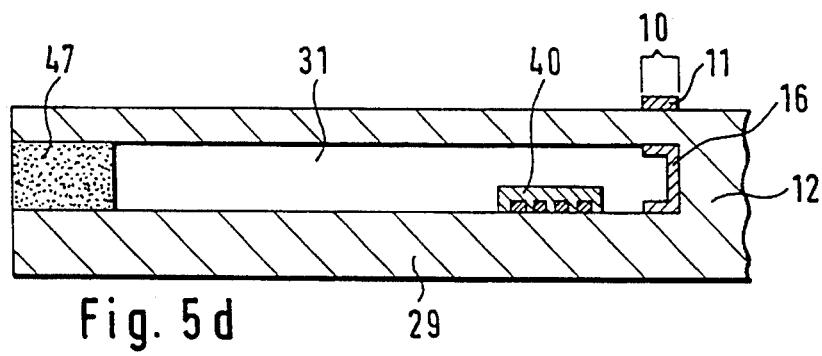
FIG. 5d shows a sectional representation through a discrete sensor consisting of a calorimetric gas sensor and an $O_2$ pump cell.

The sensor in accordance with FIG. 5d, in which in a manner similar to the embodiment in FIG. 3a the calorimetric gas sensor 40 is arranged at a distance s', s" in the diffusion gap 31 has a discrete design. The diffusion gap 31 is sealed at the entry, for example by means of a porous oxidation catalyst 47. The oxidation catalyst 47 serves to achieve a selectivity with respect to HC, the combustible gas components $NO_x$, $H_2$ and/or CO in the exhaust gas being burned by means of precombustion at a low temperature of, for example, 300° C. Consequently, it is only HC which burns at the calorimetric measuring element 40 at a higher temperature of, for example 500°–600° C.

Figure 5E:
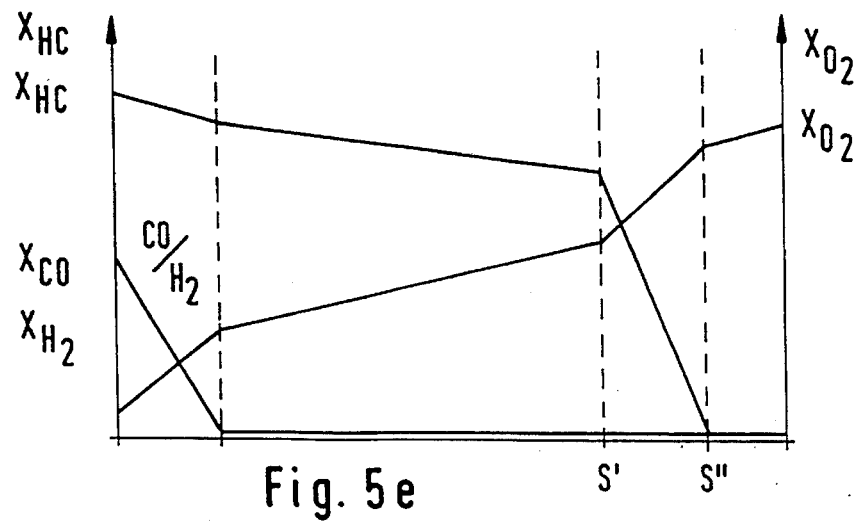
FIG. 5e shows the curve of the oxygen concentration and HC concentration against the length of the diffusion gap in accordance with the sensor in FIG. 5d.

The curve of the oxygen gradient and of the HC gradient inside the diffusion gap 31 follows from FIG. 5e. Given a sufficiently high oxygen partial pressure, it is thus ensured that the oxygen concentration at the calorimetric gas sensor 40 is above the HC concentration to be measured.

Figure 6A:
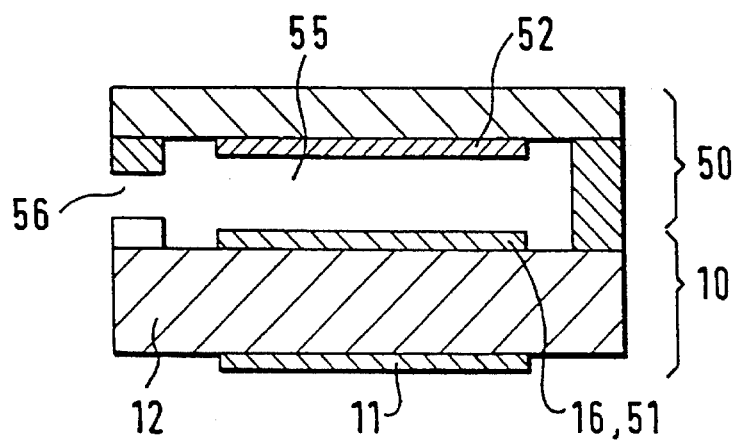
FIG. 6a shows a sectional representation through an integrated sensor consisting of an ionization detector and an $O_2$ pump cell.
Figure 6B:
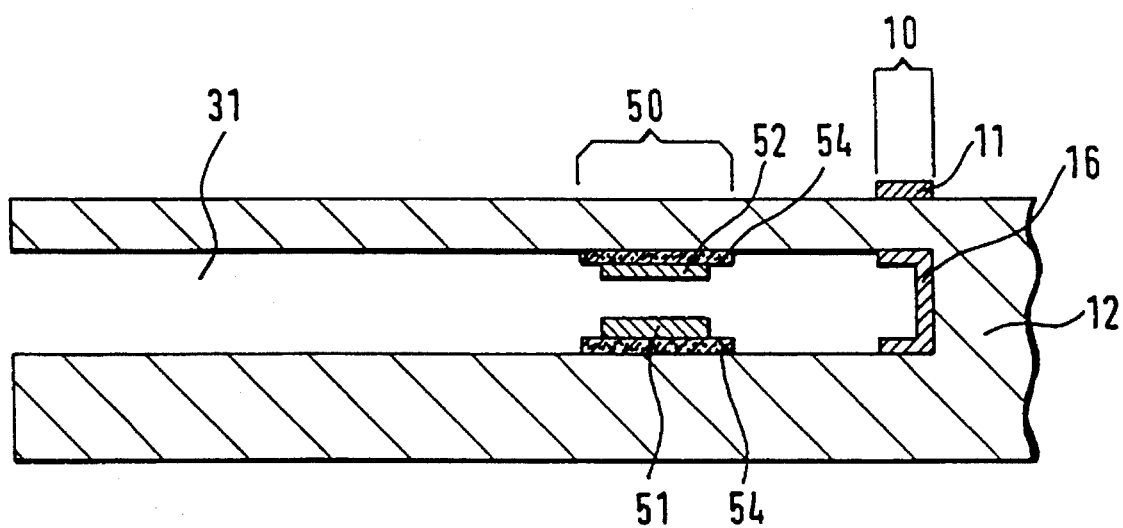
FIG. 6b shows a sectional representation through a discrete sensor consisting of an ionization detector and an $O_2$ pump cell.

The embodiments of the sensor which are represented in FIGS. 6a and 6b use an ionization detector 50 as measuring element 20. In this case, FIG. 6a shows an integrated embodiment in which the two pump electrodes 11 and 16 are arranged on the solid electrolyte carrier 12, the inner pump electrode 16 simultaneously forming an anode 51 of the ionization detector 50. A cathode 52 is situated opposite the anode 51. Formed between the anode 51 and cathode 52 is a gas chamber 55 to which the gas mixture is supplied via a measuring gas opening 56. At temperatures of, for example, 800° C., HC ions are formed at the catalytically active anode 51 during combustion and are extracted by the opposite cathode 52. The oxygen required for combustion in the exhaust gas is, as in the other exemplary embodiments, pumped directly to the anode 51 by means of the pump cell 10.

A discrete embodiment having an ionization detector is shown in FIG. 6b, the solid electrolyte carrier 12 here having the diffusion gap 31, as in the previously described discrete sensor types. The ionization detector 50 is arranged in the diffusion gap 31 at a spacing from the opening thereof. In this case, an insulating layer(s) 54 on which the anode 51 and the cathode 52 are respectively arranged are respectively applied opposite one another on the top side and the underside of the diffusion gap 31. Since in the case of the combustion reaction of HC conditions comparable to those in the case of the calorimetric sensor are present at the anode 51, the explanations already set forth in this connection are valid in the case of the considerations relating to the concentration distribution of the gases, including oxygen.

Figure 7A:
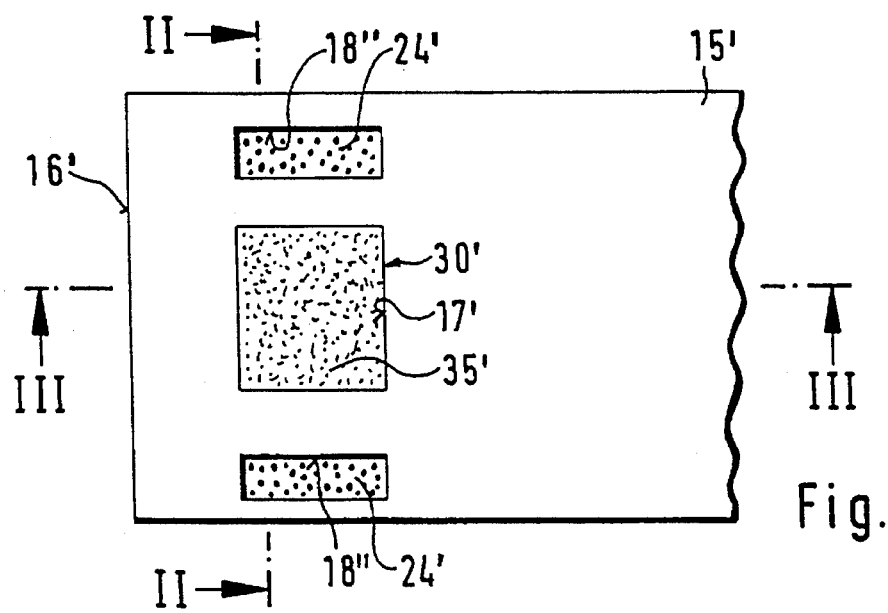
FIG. 7a shows a plan view of a section, on the measuring-gas side, of a sensor having cutouts for the entry of the measuring gas.
Figure 7B:
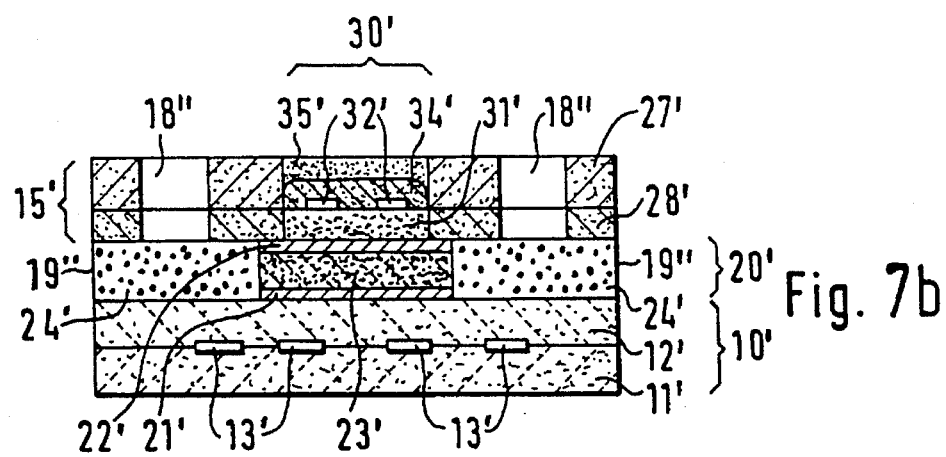
Figure 7C:
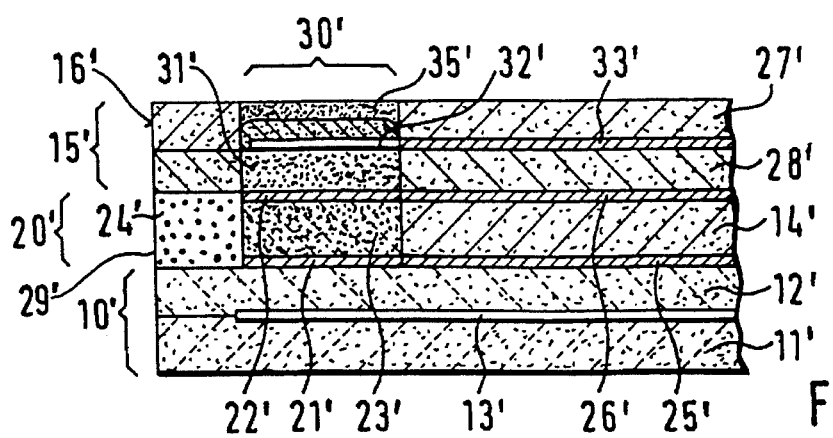

FIG. 7a shows a plan view of a section, on the measuring-gas side, of a cover foil 15 of a sensor. The sensor in accordance with FIGS. 7b and c has a ceramic carrier 10', an electrochemical oxygen pump cell 20' and a measuring element 30'. The ceramic carrier 10' has a first ceramic foil 11' made from $Al_2O_3$ and a second ceramic foil 12' likewise made from $Al_2O_3$, between which a resistance heater 13' is embedded. Arranged on the large face of the second ceramic foil 12' is an outer pump electrode 21' to which a porous oxygen-ion-conducting solid electrolyte 23' made from, for example, $Yb_2O_3$- or $Y_2O_3$-stabilized zirconium oxide is applied. For the purpose of adapting the coefficient of thermal expansion, the porous solid ! electrolyte 23' is preferably designed as a mixed ceramic made from stabilized $ZrO_2$ and $Al_2O_3$, preferably at a ratio of 1:1.

The outer pump electrode 21' is connected to a conductor track 25' guided on the second ceramic foil 12'. An electrically insulating intermediate layer 14', which expediently has the thickness of the solid electrolyte 23' and consists of $Al_2O_3$, is laid up to the solid electrolyte 23' on the second ceramic foil 12' and over the conductor track 25'. An inner pump electrode 22' is arranged on the solid electrolyte 23' opposite the outer pump electrode 21'. The inner pump electrode 22' is connected to a further conductor track 26' arranged on the intermediate layer 14'. The pump electrodes 21', 22' are cermet electrodes, preferably having a fully stabilized $ZrO_2$ support frame.

Located over the pump cell 20' is the cover foil 15', which is composed of a first insulating layer 27' and a second insulating layer 28'. The two insulating layers 27', 28' consist, for example, of $Al_2O_3$. In accordance with FIG. 7a, a cutout 17' and, to the side thereof, an opening 18" in each case are provided in the cover layer 15'. The cutout 17' is arranged such that it is situated over the pump cell 20' and reaches as far as into the inner pump electrode 22'.

The measuring element 30' is arranged in the cutout 17'. A semiconductor gas sensor is used as measuring element 30' in the present example. For this purpose, the cutout 17' a porous insulating layer 31' made, for example, from $Al_2O_3$ is applied to the inner pump electrode 22'. Two measuring electrodes 32' arranged next to one another and made, for example, of platinum are located on the porous insulating layer 31'. The two measuring electrodes 32' respectively have a measuring electrode conductor track 33' which is guided between the two insulating layers 27' and 28'. A semiconducting metal oxide layer 34' which consists, for example, of $SnO_2$ is laid over the two measuring electrodes 32'. The metal oxide layer 34' is covered by means of a porous protective layer 35' which expediently terminates flush with the surface of the second insulating layer 28'.

The two openings 18" arranged next to the cutout 17' lead to in each case one channel 19" fed laterally to the pump cell 20. The two channels 19" are expediently filled with a porous diffusion body 24' made, for example, from $ZrO_2$ for the purpose of protecting the pump cell 20'. It is equally conceivable likewise to provide the openings 18" with such a porous diffusion body. The pump cell 20' is set back from the narrow front side 16' of the sensor, resulting additionally in formation towards the front side 16' of a front channel 29' to the pump cell 20', which channel is likewise filled with the diffusion body 24'. However, it is also conceivable, on the other hand, to design the channels 19" and 29' without a filling.

In order to operate the sensor, a pumping voltage is applied to the pump electrodes 21', 22', and a constant oxygen partial pressure is set at the inner pump electrode 22' by means of a known control circuit such as is described, for example, in the SAE publication 86 04 08, with the result that in accordance with the invention the oxygen is present in excess with respect to the gas components to be measured. For example, the oxygen partial pressure is selected to be between 2 and 10% of the total pressure of the measuring gas. The constant oxygen partial pressure also corresponds to the oxygen partial pressure present at the measuring element 30'.

One way of operating the sensor is to immerse the pump cell 20' and the measuring element 30' in the measuring gas. In this case, the pump cell 20' pumps off molecular oxygen or oxygen from oxygen-containing compounds from the measuring gas via the outer pump electrode 21'. It is, however, equally conceivable to bring only the measuring element 30' into contact with the measuring gas and to expose the pump cell 20' with the channels 19', 29' and the openings 18' to a reference gas from which the oxygen has been pumped off.

The sensor types described are preferably designed using thick film technology. The screen-printing technique normally used for this purpose is satisfactorily known. Moreover, the sensor types described are expediently embodied with the integrated heater described in connection with the embodiment in FIG. 2d and whose detailed representation was dispensed with. It is, furthermore, conceivable to use other materials for the layer construction. For example, the layer system can be built up on a ceramic substrate.

It is, however, equally conceivable to design individual layers as foils, so that the sensor is constructed overall as a laminate composite.

We claim:

1. Sensor for determining gas components and/or gas concentrations in gas mixtures, in particular of CO, $NO_x$ and HC in exhaust gases of internal combustion engines, said sensor comprising: a measuring element having a sensitive regional; a pump cell with pump electrodes which are arranged on a solid electrolyte, with the pump electrodes causing a transfer of oxygen to the measuring element by utilizing the oxygen ion conduction of the solid electrolyte; and, a diffusion path for the gas mixture and the oxygen pumped by the pump cell, with the gas mixture and the pumped oxygen being carried to the sensitive region of the measuring cell via the diffusion path; and wherein: an electrode of the pump cell is disposed in the diffusion path and is arranged in the direction of the gas mixture downstream of the sensitive region of the measuring element so that a concentration gradient of the gas component to be determined and an oxygen concentration gradient are formed in the diffusion path and run counter to one another; and, the measuring element is arranged in the diffusion path relative to the gradients such that the oxygen concentration present in the sensitive region of the measuring element is larger than the concentration of the gas component to be determined in the sensitive region so that the measuring element is located in a region of high sensitivity relative to the gas component or gas components to be determined.

2. Sensor according to claim 1 wherein the gas concentration of the component to be measured is set such that a change in gas concentration delivers a change in the sensor signal which is substantially greater than the change in the sensor signal caused by the change in oxygen concentration.

3. Sensor according to claim 1 wherein the maximum concentration, occurring on the sensitive region of the measuring element, of the gas component to be determined is set approximately to the stoichiometric value with regard to the oxygen concentration and does not, however, exceed said value of the oxygen concentration, with the result that the concentration of the gas component to be determined delivers a maximum sensor signal.

4. Sensor according to claim 1, wherein the pump cell has an inner and an outer pump electrode, the measuring element forms an integrated layer system with the pump cell, and the diffusion path is formed by at least one porous layer, with the gradient of the gas component to be determined and the oxygen gradient build up extending respectively in opposite directions in the porous layer.

5. Sensor according to claim 4, wherein a semiconductor gas sensor made from a porous semiconducting metal oxide layer forming the sensitive region is provided as the measuring element.

6. Sensor according to claim 4, wherein a porous insulating layer which forms the diffusion path is arranged on the inner pump electrode, and a semiconducting metal oxide layer of a semiconductor gas sensor, which forms the measuring element, is arranged on the insulating layer.

7. Sensor according to claim 4, wherein the measuring element is an electrochemical measuring cell having an $O^{-2}$-conducting solid electrolyte on which a measuring electrode and a reference electrode are arranged, with the $O^{-2}$-conducting solid electrolyte being constructed in a porous fashion and forming the diffusion path.

8. Sensor according to claim 4, wherein the measuring element is a calorimetric sensor which is arranged on the solid electrolyte carrier, at least two resistors are provided, one of the resistors is embedded in a catalytically active layer, with the result that the temperature of this resistor varies, and the other resistor is assigned to a catalytically inactive layer.

9. Sensor according to claim 8, wherein the catalytically active layer is embodied in a porous fashion and forms the diffusion path.

10. Sensor according to claim 8, wherein a porous insulating layer which forms the diffusion path is arranged on the inner pump electrode.

11. Sensor according to claim 4, wherein the measuring element is an ionization detector having a catalytically active anode arranged in an ionization chamber and a cathode, where by at relatively high temperatures the anode forms positive ions which the cathode extracts by means of an extraction voltage, and the ionization chamber forms the diffusion path.

12. Sensor according to claim 1, wherein the pump cell and the measuring element are arranged spatially separated from one another and are interconnected via a diffusion gap, and the diffusion gap is exposed to the gas mixture by an opening, with the diffusion gap forming the diffusion path, and the oxygen gradient and the gradient of the gas component to be determined building up and extending respectively in opposite directions in the diffusion gap.

13. Sensor according to claim 12, wherein the pump cell has an inner and an outer pump electrode and is arranged at the closed end of the diffusion gap, and the measuring element is arranged in the diffusion gap.

14. Sensor according to claim 12, wherein the measuring element is a semiconductor gas sensor which is arranged on the large face of the diffusion gap introduced into the solid electrolyte.

15. Sensor according to claim 12, wherein the measuring element is an electrochemical measuring cell which is arranged on the large face of the diffusion gap introduced into the solid electrolyte.

16. Sensor according to claim 15, wherein the pump cell has an inner pump electrode and an outer pump electrode, the inner pump electrode simultaneously forms a reference electrode of the measuring cell, and a measuring electrode is arranged on the large face of the diffusion gap.

17. Sensor according to claim 12, wherein the measuring element is a calorimetric gas sensor, which is arranged on the large face of the diffusion gap introduced into the solid electrolyte.

18. Sensor according to claim 12, wherein the measuring element is an ionization detector which is arranged in the diffusion gap such that a catalytic anode and a cathode are situated opposite one another.

19. Sensor according to claim 12, wherein the opening on the exhaust-gas side of the diffusion gap is sealed by an oxidation catalyst which is permeable only to selected gas components.

20. Sensor according to claim 1, wherein the solid electrolyte of the pump cell is constructed in a porous fashion.

21. Sensor according to claim 20, wherein at least one diffusion channel which leads laterally to the porous solid electrolyte is provided for the oxygen to be pumped.

22. Sensor according to claim 20, wherein the diffusion channel is filled with a diffusion body.

23. Sensor according to claim 20, wherein the porous solid electrolyte consists of a mixed ceramic made from stabilized $ZrO_2$ and $Al_2O_3$, preferably in the ration of 1:1.

24. Sensor according to claim 20, wherein a the substrate is provided with at least one cover layer in which a cutout is provided over the pump cell, and the measuring element is arranged in the cutout.

25. Sensor according to claim 24, wherein at least one opening which leads to at least one of the lateral diffusion channels is provided on the cover layer.

26. Sensor according to claim 25, wherein a porous diffusion layer which is laid over the pump electrode and over which the measuring element is located, is provided in the cutout so that it is possible for the oxygen to diffuse from the pump cell to the measuring element via the porous layer.

27. Sensor according to claim 1, wherein a porous layer which forms a diffusion barrier is applied to the measuring element.

* * * * *